United States Patent
Tian et al.

(10) Patent No.: US 12,235,257 B2
(45) Date of Patent: Feb. 25, 2025

(54) METHOD OF ANALYZING INFLUENCING FACTORS OF CONTRIBUTION RATE OF ELASTIC ENERGY OF TOP PLATE DURING CATASTROPHE OF COAL BODY

(71) Applicant: SHANDONG UNIVERSITY OF SCIENCE AND TECHNOLOGY, Qingdao (CN)

(72) Inventors: Chenglin Tian, Qingdao (CN); Qianting Hu, Qingdao (CN); Haitao Sun, Qingdao (CN); Xusheng Zhao, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 0 days.

(21) Appl. No.: 18/571,358

(22) PCT Filed: Jan. 9, 2023

(86) PCT No.: PCT/CN2023/071382
§ 371 (c)(1),
(2) Date: Dec. 18, 2023

(87) PCT Pub. No.: WO2023/138431
PCT Pub. Date: Jul. 27, 2023

(65) Prior Publication Data
US 2024/0361294 A1    Oct. 31, 2024

(30) Foreign Application Priority Data
Jan. 20, 2022  (CN) .......................... 202210063523.5

(51) Int. Cl.
*G01N 33/22*    (2006.01)
*G01N 3/00*     (2006.01)
*G06F 30/20*    (2020.01)

(52) U.S. Cl.
CPC ............. *G01N 33/222* (2013.01); *G01N 3/00* (2013.01); *G01N 2203/0032* (2013.01)

(58) Field of Classification Search
CPC ................... G01N 33/222; G01N 3/00; G01N 2203/0032; G01N 3/12; G01N 33/24;
(Continued)

(56) References Cited

U.S. PATENT DOCUMENTS

| | | | |
|---|---|---|---|
| 2017/0235016 A1* | 8/2017 | Prioul | G01N 29/04 73/152.01 |
| 2017/0268970 A1* | 9/2017 | Heinlein | G01N 3/08 |
| 2021/0263003 A1* | 8/2021 | Wang | G01N 3/08 |

FOREIGN PATENT DOCUMENTS

| | | |
|---|---|---|
| CN | 104850897 A | 8/2015 |
| CN | 109345119 A | 2/2019 |
| CN | 111665135 A | 9/2020 |

OTHER PUBLICATIONS

ISA (CNIPA), ISR of PCT/CN2023/071382, Feb. 9, 2023.
ISA (CNIPA), Written Opinion of PCT/CN2023/071382, Feb. 9, 2023.

* cited by examiner

*Primary Examiner* — Brandi N Hopkins
(74) *Attorney, Agent, or Firm* — Hemisphere Law, PLLC; Zhigang Ma

(57) ABSTRACT

A method of analyzing influencing factors of a contribution rate of elastic energy of a top plate during catastrophe of a coal body; the specific steps are: taking a core on site and processing the core into a standard test piece; obtaining, by means of an indoor mechanical test, elastic moduli of the top plate and of gas-containing coal, respectively; substituting the obtained elastic moduli and thicknesses of the top plate and of the gas-containing coal into a calculation formula so as to obtain the contribution rate of the elastic energy of the (Continued)

top plate; and analyzing the influence of the contribution rate of the elastic energy of the top plate in the two situations of configuring the same thickness ratio and a different elastic modulus ratio and the same elastic modulus ratio and a different thickness ratio. The method has important theoretical significance and practical engineering value.

1 Claim, 3 Drawing Sheets

(58) Field of Classification Search
CPC .......... G01N 1/286; G01N 1/36; G01N 13/02; G01N 2001/021; G01N 2001/366; G01N 2013/0208
See application file for complete search history.

METHOD OF ANALYZING INFLUENCING FACTORS OF CONTRIBUTION RATE OF ELASTIC ENERGY OF TOP PLATE DURING CATASTROPHE OF COAL BODY

TECHNICAL FIELD

The present disclosure relates to a method of analyzing influencing factors of a contribution rate of elastic energy of a top plate during catastrophe of a coal body.

BACKGROUND

China is the largest producer and consumer of coal in the world, and coal plays an important role in the energy structure of China. Although a series of corresponding prevention and control measures have been taken, mine dynamic disasters involving coal and rock gas still occur. In the final analysis, the understanding of the mechanism of coal and rock gas disasters is not clear and perfect enough.

At present, the research on mine dynamic disasters (coal and gas outburst, rock burst) usually focuses on the role of coal itself and gas. On the one hand, the related research conducts analysis only based on the stress and gas situation of the coal seam and directly ignores the elastic energy of the top plate. On the other hand, a rough estimate is only given, but in fact, there is no reasonable calculation and evaluation method for the participating elastic energy of the top plate, especially under deep mining conditions. The problems of high ground stress, high temperature and high gas in deep mining increase the risk of coal and gas outburst and the coal and rock impact, which further increases the probability of complex coal and rock dynamic disasters in some high-gas mines and coal and gas outburst mines. Such disasters not only show some characteristics of coal and gas outburst, but also some characteristics of rock burst. The two dynamic disasters coexist, influence and compound with each other. At the same time, the deep composite coal and rock dynamic disaster is a complex mechanical process under the dual effects of "high stress (ground stress) and dynamic disturbance (depressurized mining)". Many factors are intertwined in the process of disaster occurrence, which may lead to mutual inducement, mutual reinforcement or "resonance" effect in the process of accident preparation, occurrence and development. Thus, the mechanism of composite dynamic disasters is more complicated. It is more important to know the specific participation role of elastic energy of rocks in the process of disasters.

Based on this, the present disclosure provides a method of analyzing influencing factors of a contribution rate of elastic energy of a top plate during catastrophe of a coal body.

SUMMARY

Aiming at the shortcomings of the prior art, the present disclosure provides a method of analyzing influencing factors of a contribution rate of elastic energy of a top plate during catastrophe of a coal body, which establishes an expression of the contribution rate of the elastic energy of the top plate and analyzes its influencing factors, and provides a certain theoretical basis for accurate prevention and control of coal and rock gas dynamic disasters.

A method of analyzing influencing factors of a contribution rate of elastic energy of a top plate during catastrophe of a coal body is provided, including the following steps:

Step 1, calculating the contribution rate of the elastic energy of the top plate:

($S_1$) obtaining gas-containing coal seam gas pressure p;

($S_2$) according to a drilling histogram, obtaining gas-containing coal seam thickness $h_c$ and top plate thickness $h_r$;

($S_3$) coring the gas-containing coal seam and the top plate, processing the core into a standard test piece, and obtaining, by means of a mechanical test, elastic moduli $E_r$ of the top plate and elastic moduli $E_c$ of the coal seam under the influence of the gas pressure P, respectively;

($S_4$) calculating the contribution rate η of the elastic energy of the top plate according to the data obtained in step ($S_1$) to step ($S_3$)

$$\eta = \lambda \cdot E_c h_r / (E_c h_r + E_r h_c) \times 100\% \quad (1)$$

in formula (1), λ is a correction factor, and 0<λ≤1; $h_r$ and $h_c$, $E_r$ and $E_c$ satisfy formula (2):

$$\begin{cases} h_r = m h_c \\ E_r = n E_c \end{cases} \quad (2)$$

in formula (2), m>0 and n>0; substituting formula (2) into formula (1) to obtain:

$$\eta = \lambda \cdot n/(m+n) \times 100\% \quad (3)$$

Step 2, analyzing the influence factor of the contribution rate of the elastic energy of the top plate:

according to formula (3), analyzing the influence of m and n on the contribution rate η of the elastic energy of the top plate, wherein the following two situations are configured:

situation 1: the influence of the same m but different n on η;

situation 2: the influence of the same n but different m on η;

obtaining the comprehensive influence of m and n on the contribution rate η of the elastic energy of the top plate according to situation 1 and situation 2 respectively.

The present disclosure has the following beneficial effects.

1) According to the actual situation on site, the present disclosure puts forward a method of analyzing influencing factors of a contribution rate of elastic energy of a top plate during catastrophe of a coal body, which establishes an expression and provides a certain theoretical basis for accurate prevention and control of coal and rock gas dynamic disasters.

2) It is simple and convenient to calculate the contribution rate of the elastic energy of the top plate provided by the present disclosure, which can be obtained only by measuring the relevant mechanical indexes of a coal and rock monomer containing gas.

3) At the same time, the present disclosure puts forward the influencing factors of the contribution rate of the elastic energy and carries out relevant analysis based on this, so as to further clarify and quantify the main factors influencing the contribution rate of the elastic energy.

4) The present disclosure fully considers the influence of the elastic energy of the top plate in coal and rock dynamic disasters and has important theoretical significance and practical engineering value. Moreover, the present disclosure has positive significance for the prediction and prevention of mining-induced rock burst-coal and gas outburst and other complex dynamic mining disasters.

DETAILED DESCRIPTION OF THE EMBODIMENTS

In order to fully embody the features and advantages of the present disclosure, the present disclosure will be described in detail with reference to the attached drawings and specific embodiments.

Figure 1:
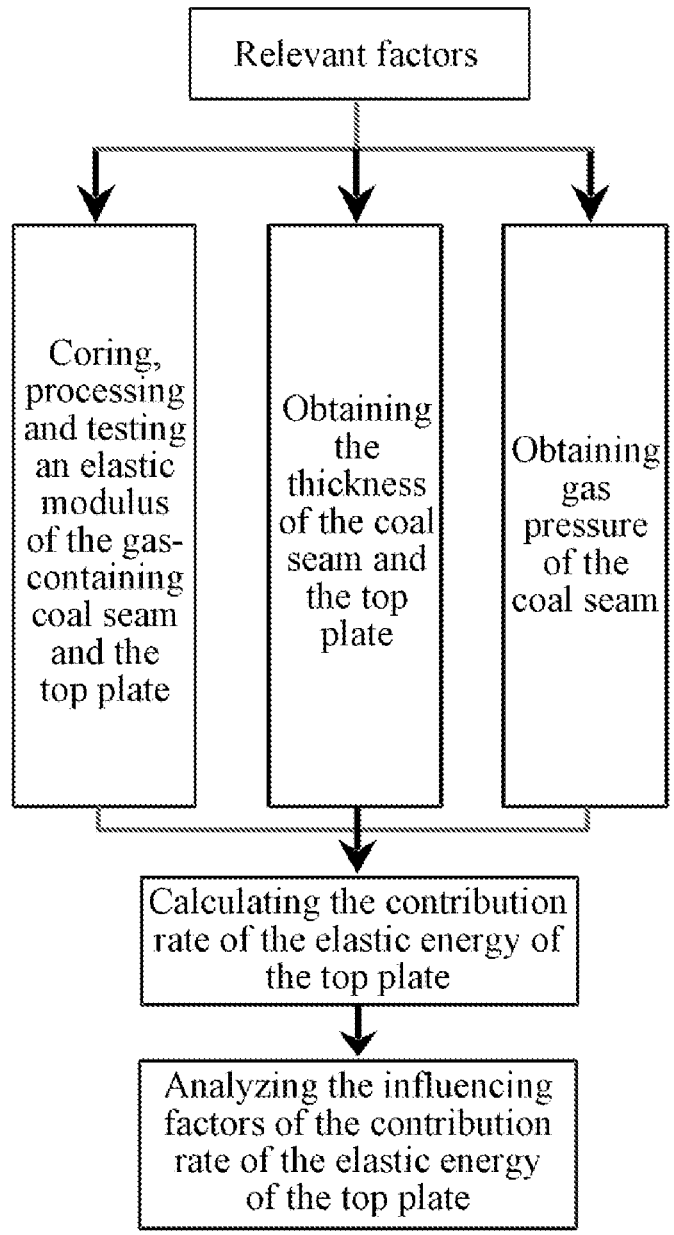
FIG. 1 is a flow chart of a method of analyzing influencing factors of a contribution rate of elastic energy of a top plate during catastrophe of a coal body.
Figure 2:
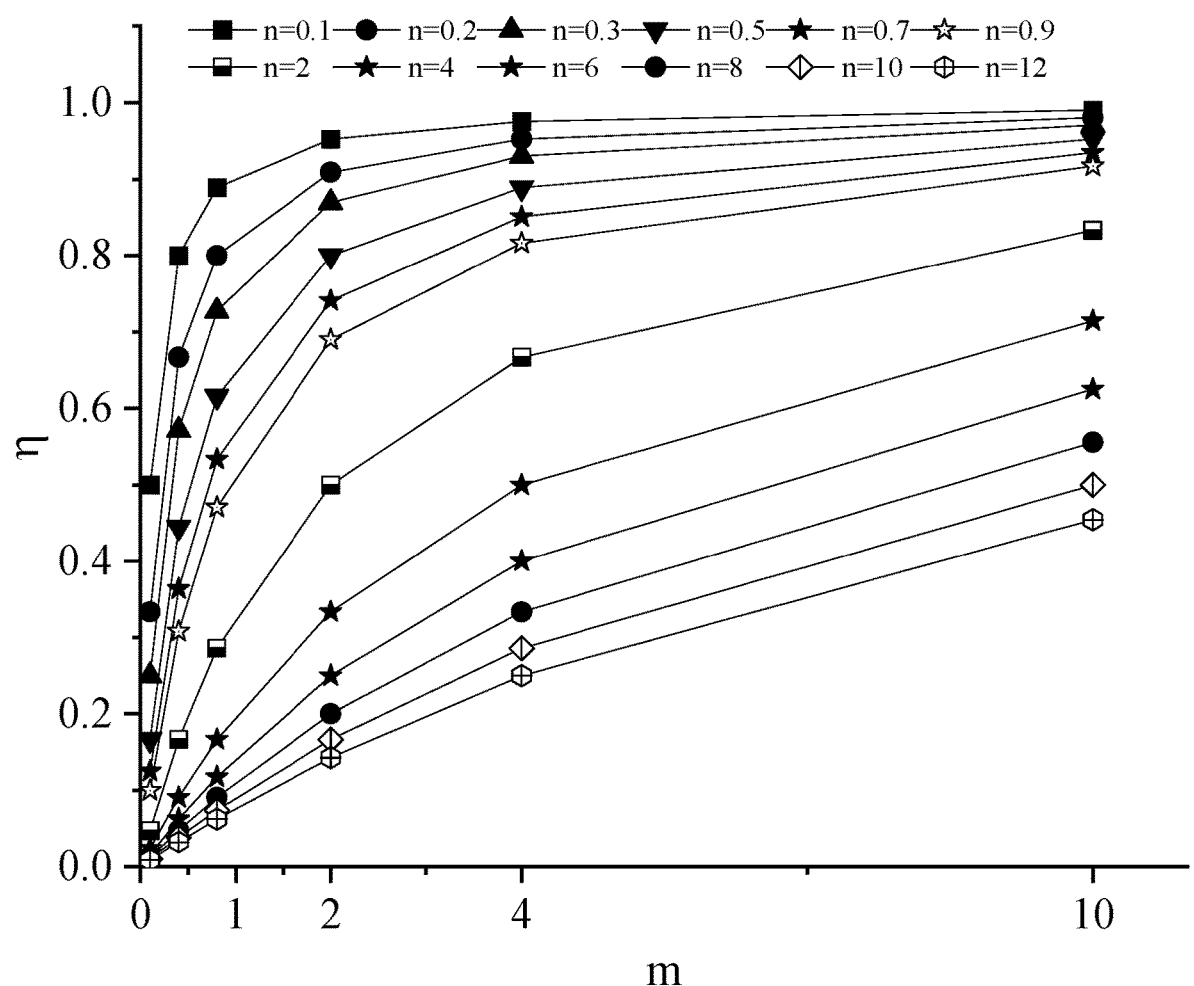
FIG. 2 is an influence distribution diagram of parameter m on η according to an embodiment of the present disclosure.
Figure 3:
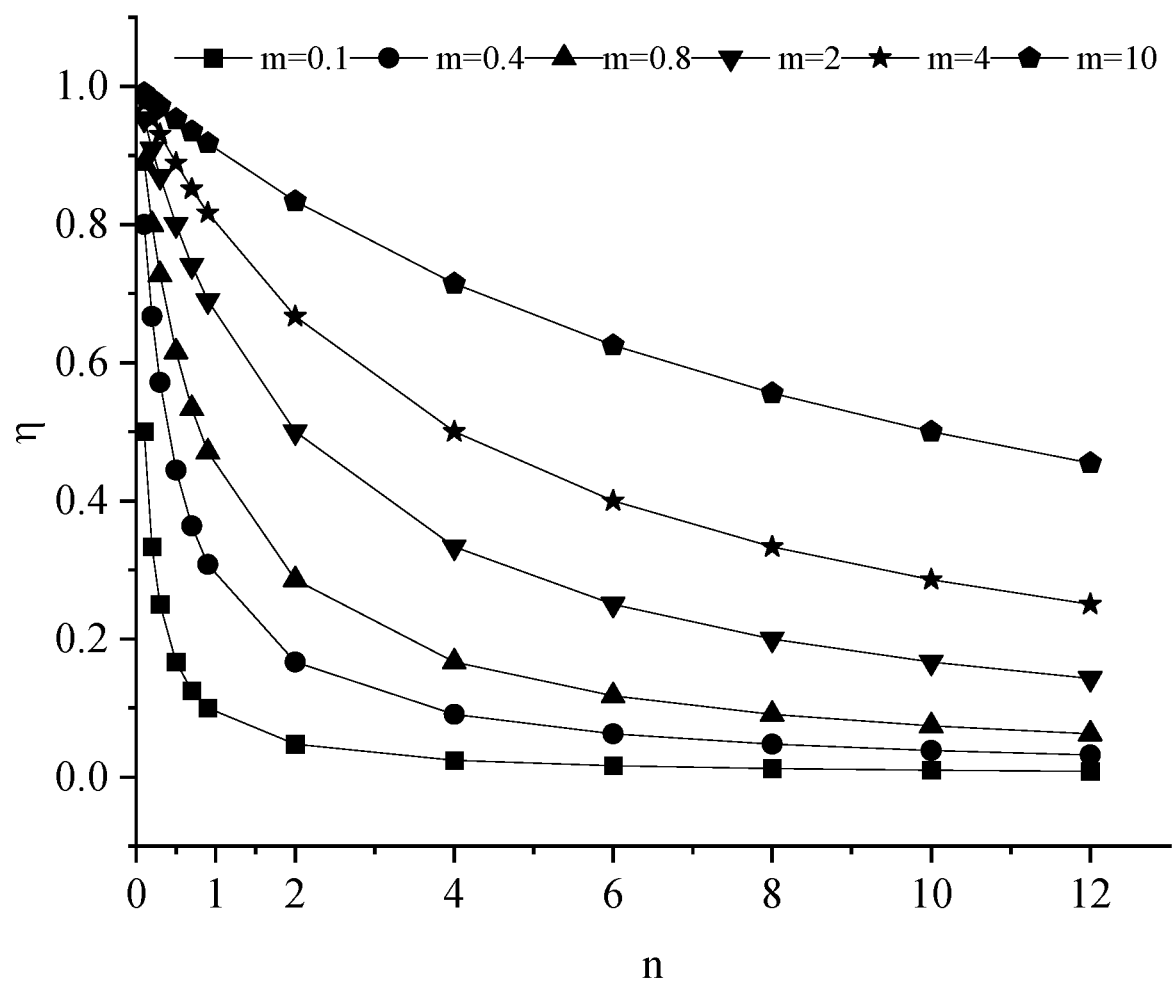
FIG. 3 is an influence distribution diagram of parameter n on η according to an embodiment of the present disclosure.

As shown in FIG. 1 to FIG. 3, a method of analyzing influencing factors of a contribution rate of elastic energy of a top plate during catastrophe of a coal body is provided, including the following steps:

Step 1, calculating the contribution rate of the elastic energy of the top plate:
($S_1$) obtaining gas-containing coal seam gas pressure p;
($S_2$) according to a drilling histogram, obtaining gas-containing coal seam thickness $h_c$ and top plate thickness $h_r$;
($S_3$) coring the gas-containing coal seam and the top plate, processing the core into a standard test piece, and obtaining, by means of a mechanical test, elastic moduli $E_r$ of the top plate and elastic moduli $E_c$ of the coal seam under the influence of the gas pressure p, respectively;
($S_4$) calculating the contribution rate η of the elastic energy of the top plate according to the data obtained in step ($S_1$) to step ($S_3$)

$$\eta = \lambda \cdot E_c h_r / (E_c h_r + E_r h_c) \times 100\% \quad (1)$$

in formula (1), λ is a correction factor, and 0<λ≤1 $h_r$ and $h_c$, $E_r$ and $E_c$ satisfy formula (2):

$$\begin{cases} h_r = mh_c \\ E_r = nE_c \end{cases} \quad (2)$$

in formula (2), m>0 and n>0; substituting formula (2) into formula (1) to obtain:

$$\eta = \lambda \cdot n/(m+n) \times 100\% \quad (3)$$

Step 2, analyzing the influence factor of the contribution rate of the elastic energy of the top plate:

according to formula (3), analyzing the influence of m and n on the contribution rate η of the elastic energy of the top plate, wherein the following two situations are configured:
situation 1: the influence of the same m but different n on η;
situation 2: the influence of the same n but different m on η;
obtaining the comprehensive influence of m and n on the contribution rate η of the elastic energy of the top plate according to situation 1 and situation 2 respectively.

EMBODIMENT

In order to further analyze the specific influence of m and n on η, the analysis is carried out within the m range of [0.1,10] and the n range of [0.1,12], and the value of λ is 1, which is divided into the following two situations.

Situation 1: the influence of the same layer thickness m but different elastic modulus n on η.

It can be seen from FIG. 2 that when the ratio of thickness of the rock to the coal is the same (equal to m) in a two-body combined structure, the greater the ratio n of the elastic modulus of the rock to the coal, the smaller the contribution rate η of the elastic energy of the top plate. However, the overall contribution rate η of the elastic energy of the top plate increases with the increase of the ratio m of the thickness of the rock to the coal.

Situation 2: the influence of the same n but different m on the contribution rate η of the elastic energy of the top plate.

It can be seen from FIG. 3 that when the ratio of the elastic modulus of the rock to the coal is the same (equal to n) in a two-body combined structure, the greater the ratio m of the thickness of the rock to the coal, the greater the contribution rate η of the elastic energy of the top plate. However, the overall contribution rate η of the elastic energy of the top plate decreases with the increase of the ratio n of the elastic modulus of the rock to the coal, but the decreasing trend gradually slows down.

Although the specific embodiment of the present disclosure has been described with the attached drawings, it is not a limitation on the scope of protection of the present disclosure. Those skilled in the art should understand that on the basis of the technical scheme of the present disclosure, various modifications or transformations that can be made by those skilled in the art without creative labor are still within the scope of protection of the present disclosure.

What is claimed is:
1. A method of analyzing influencing factors of a contribution rate of elastic energy of a top plate during catastrophe of a coal body, comprising the following steps:
Step 1, calculating the contribution rate of the elastic energy of the top plate:
($S_1$) obtaining gas-containing coal seam gas pressure p;
($S_2$) according to a drilling histogram, obtaining gas-containing coal seam thickness $h_c$ and top plate thickness $h_r$;
($S_3$) coring the gas-containing coal seam and the top plate, processing the core into a standard test piece, and obtaining, by means of a mechanical test, elastic moduli $E_r$ of the top plate and elastic moduli $E_c$ of the coal seam under the influence of the gas pressure p, respectively;
($S_4$) calculating the contribution rate n of the elastic energy of the top plate according to the data obtained in step ($S_1$) to step ($S_3$),

$$\eta = \lambda \cdot E_c h_r / (E_c h_r + E_r h_c) \times 100\% \qquad (1)$$

in formula (1), A is a correction factor, and $0<\lambda\leq 1$; $h_r$ and $h_c$, $E_r$ and $E_c$ satisfy formula (2):

$$\begin{cases} h_r = m h_c \\ E_r = n E_c \end{cases} \qquad (2)$$

in formula (2), m>0 and n>0; substituting formula (2) into formula (1) to obtain:

$$\eta = \lambda \cdot n/(m+n) \times 100\% \qquad (3)$$

Step 2, analyzing the influence factor of the contribution rate of the elastic energy of the top plate:
according to formula (3), analyzing the influence of m and n on the contribution rate η of the elastic energy of the top plate, wherein the following two situations are configured:
situation 1: the influence of the same m but different n on η;
situation 2: the influence of the same n but different m on η;
obtaining the comprehensive influence of m and n on the contribution rate η of the elastic energy of the top plate according to situation 1 and situation 2 respectively.

* * * * *